United States Patent [19]

Chester et al.

[11] Patent Number: 4,663,492

[45] Date of Patent: May 5, 1987

[54] ACTIVE ZEOLITE CATALYSTS OF IMPROVED STABILITY FOR PRODUCING GASOLINE FROM METHANOL

[75] Inventors: Arthur W. Chester; Yung F. Chu, both of Cherry Hill, N.J.

[73] Assignee: Mobil Oil Corporation, New York, N.Y.

[21] Appl. No.: 872,359

[22] Filed: Jun. 9, 1986

Related U.S. Application Data

[63] Continuation-in-part of Ser. No. 685,194, Dec. 21, 1984, Pat. No. 4,594,146, which is a continuation-in-part of Ser. No. 539,497, Oct. 6, 1983, Pat. No. 4,522,929, which is a continuation-in-part of Ser. No. 346,440, Feb. 8, 1982, Pat. No. 4,429,176.

[51] Int. Cl.$^4$ .............................................. C07C 11/20
[52] U.S. Cl. ................................... 585/408; 585/640; 585/733
[58] Field of Search ..................... 585/408, 640, 733

[56] References Cited

U.S. PATENT DOCUMENTS

| | | | |
|---|---|---|---|
| 3,965,209 | 6/1976 | Butter et al. | 260/671 M |
| 3,969,426 | 7/1976 | Owen et al. | 260/668 R |
| 4,236,996 | 12/1980 | Tabak et al. | 208/134 |
| 4,326,994 | 4/1982 | Haag et al. | 252/455 Z |
| 4,429,176 | 1/1984 | Chester et al. | 585/481 |
| 4,522,929 | 6/1985 | Chester et al. | 502/77 |

Primary Examiner—Curtis R. Davis
Attorney, Agent, or Firm—Alexander J. McKillop; Michael G. Gilman; L. G. Wise

[57] ABSTRACT

A feedstock of low molecular weight oxygenates such as methanol and/or dimethylether is contacted with a mildly presteamed or hydro-thermally treated zeolite catalyst in a reaction zone to produce liquid hydrocarbons in the gasoline boiling range. The pretreated zeolite catalyst has an α-value (acid cracking activity) substantially the same as the α-value of fresh unsteamed catalyst and shows increased stability and resistance to aging under oxygenate conversion conditions of elevated temperature and pressure.

12 Claims, 2 Drawing Figures

ACTIVE ZEOLITE CATALYSTS OF IMPROVED STABILITY FOR PRODUCING GASOLINE FROM METHANOL

CROSS REFERENCE TO RELATED APPLICATIONS

This application is a continuation-in-part of U.S. Ser. No. 685,194, filed on Dec. 21, 1984, now U.S. Pat. No. 4,594,146, which is a continuation-in-part of application Ser. No. 539,497, filed on Oct. 6, 1983, now U.S. Pat. No. 4,522,929, which is a continuation-in-part of application Ser. No. 346,440, filed on Feb. 8, 1982, now U.S. Pat. No. 4,429,176.

BACKGROUND OF THE INVENTION

1. Field of the Invention

This invention relates to a process for presteaming or hydro-thermally treating a zeolite catalyst so as to substantially retain its initial activity and to a process for the preparation of superior zeolite catalysts to be used in high pressure methanol-to-gasoline (MTG) reactions.

2. Background of the Invention

Acid-catalyzed methanol-to-gasoline (MTG) reactions conducted at elevated temperatures and pressures result in the rapid degeneration of catalyst activity. It is well known in the art that mild-to-severely steamed zeolite catalysts provide improved stability but suffer from lowered activity in acid-catalyzed reactions.

Much of the prior art in this area deals with severely steamed zeolite catalysts in reactions such as xylene isomerization.

U.S. Pat. No. 4,224,141 (Morrison et al) discloses a xylene isomerization process with a catalyst steamed at a temperature in excess of 538° C. (1000° F.) for a period of time longer than 15 hours. The resulting catalyst is highly stable, but suffers from lowered activity.

U.S. Pat. No. 4,188,282 (Tabak et al) discloses a xylene isomerization process using a catalyst with a silica/alumina ratio of at least 200. The catalyst is severely steamed to a lowered activity as described in U.S. Pat. No. 4,016,218 (Haag et al) and U.S. Pat. No. 3,965,209 (Butter et al).

U.S. Pat. No. 4,236,996 (Tabak et al) discloses a xylene isomerization process wherein the catalyst is steamed at a high temperature to reduce the activity such that the conversion reaction temperature must be increased by at least 10° C. to equal the conversion capability of an unsteamed zeolite.

U.S. Pat. No. 3,965,209 (Butter et al) discloses a process whereby the zeolite is steamed to reduce the alpha activity to less than 500 by treating the zeolite in a steam atmosphere at a temperature of from 250° C. to about 1000° C. (526° F. to about 2026° F.) for from about ½ hour to 100 hours.

U.S. Pat. No. 4,326,994 (Haag et al) discloses a process whereby a zeolite is steamed to activate or increase its alpha activity.

U.S. Pat. No. 3,969,426 (Owen et al) discloses a process for converting methanol to an aliphatic product and highly aromatic product boiling in the gasoline boiling range over a ZSM-5 crystalline zeolite.

U.S. Pat. No. 4,326,994 (Haag et al) discloses acid zeolite catalysts of increased activity which are prepared by contacting the acid catalysts with water for a sufficient time, temperature, and water partial pressure to bring about the enhanced activity. The contact water can be produced in situ as, for example, in alcohol dehydration to produce olefins and steam (column 7, line 56).

The present invention differs from the U.S. Pat. No. 4,326,994 patent with respect to the reaction conditions which the methanol feed undergoes. The U.S. Pat. No. 4,326,994 discloses conditions of moderate temperature, pressure, and liquid hourly space velocity to produce olefins and steam from a methanol feedstock; whereas the present invention relates to the process of contacting a methanol feedstock under oxygenate reaction conditions of elevated temperature and pressure and in the presence of a steamed or thermally treated catalyst of improved stability yet similar activity as the untreated catalyst to yield a predominantly gasoline range liquid hydrocarbon product.

There are references which disclose the use of mildly steamed zeolite catalysts in methanol-to-gasoline (MTG) conversion reactions.

U.S. Pat. No. 4,429,176 (Chester et al) incorporated herein by reference, discloses the use of a mildly presteamed catalyst in a methanol-to-gasoline (MTG) process (Column 8, line 46). The pretreated catalyst has increased stability over the fresh catalyst.

U.S. Pat. No. 4,522,929 (Chester et al) incorporated herein by reference, discloses the use of a mildly presteamed catalyst in a methanol-to-gasoline (MTG) process (column 8, line 43). The pretreated catalyst has increased stability over the fresh catalyst.

U.S. patent application Ser. No. 685,194, allowed, incorporated herein by reference, discloses the use of a mildly presteamed catalyst in a methanol-to-gasoline (MTG) process. The pretreated catalyst retains the activity of the fresh catalyst but has improved aging characteristics.

SUMMARY OF THE INVENTION

The present invention provides a process for converting a feedstock comprising lower aliphatic $C_1$–$C_4$ oxygenates such as alcohols, ethers, carboxylates, and ketones and their acetals to conversion products comprising hydrocarbon compounds in the gasoline boiling range which comprises contacting the feedstock at conversion conditions of high temperature and pressure with a catalyst comprising a zeolite having a silica/alumina ratio greater than 12 and a constraint index of 1 to 12, and wherein said zeolite is steamed in its fresh state under controlled conditions of temperature, time and steam partial pressure so as to initially increase the α-activity of said catalyst and produce a steamed catalyst having a peak α-activity, and subsequently reduce the α-activity from the peak α-activity to an α-activity substantially the same as the α-activity of the fresh catalyst and no more than 25% below the initial α-activity of the fresh catalyst.

In another embodiment, the present invention provides a process for producing liquid hydrocarbons from lower aliphatic $C_1$–$C_4$ oxygenate feedstock under elevated temperature and pressure oxygenate conversion process conditions employing an acidic ZSM-5 type aluminosilicate zeolite catalyst having a silica/alumina ratio of about 20:1 to 200:1 and a constraint index of about 1 to 12, and wherein said zeolite is hydro-thermally treated in its fresh state under controlled conditions of temperature and time to increase the α-activity of the fresh catalyst initially and produce a steamed catalyst having a peak α-activity, and subsequently reduce the α-activity from the peak α-activity to an α-activity substantially the same as the α-activity of the fresh catalyst and no more than 25% below the initial α-activity of the fresh catalyst, the hydro-thermal treatment being conducted in the substantial absence of lower aliphatic oxygenates. The pretreated catalyst has increased duration of stable activity and resistance to aging.

DETAILED DESCRIPTION OF THE INVENTION

Figure 1:
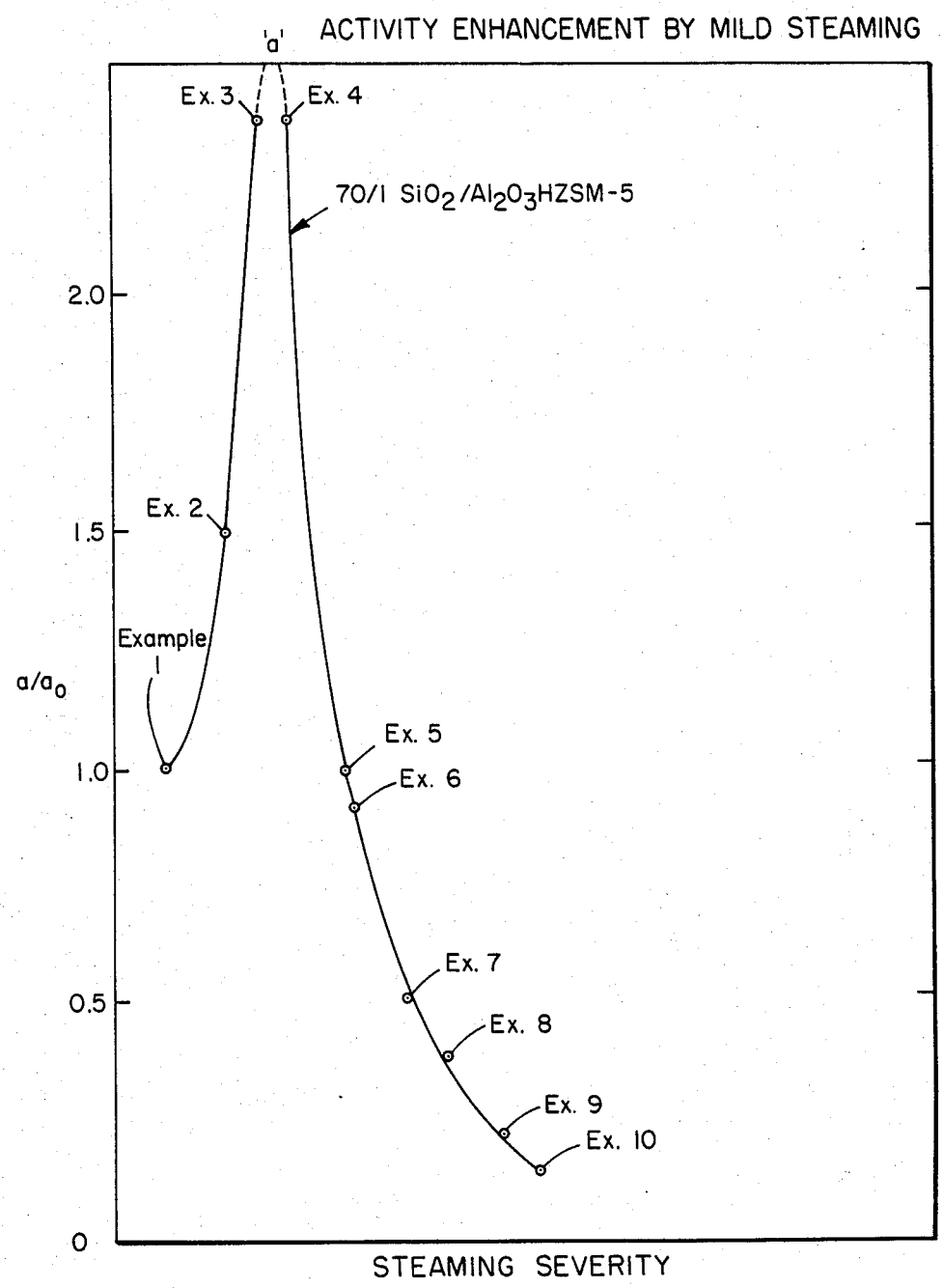
FIG. 1 illustrates the relationship of activity enhancement by mild steaming vs. steaming severity.

In a preferred invention embodiment, the process involves converting methanol, dimethylether, or mixtures thereof to gasoline range hydrocarbon products by contacting the methanol, etc. under conversion conditions with a catalyst comprising a zeolite having a silica/alumina ratio greater than 12 and a constraint index of 1 to 12. Such a methanol-to-gasoline (MTG) conversion process utilizes a catalyst which has been pretreated in a particular manner. Prior to contact with the feedstock, the zeolite-based catalyst is steamed or hydro-thermally treated at a temperature and pressure and for a period of time so as to initially increase the α-activity of the catalyst and produce a catalyst having a peak α-activity and to subsequently reduce the α-activity from the peak α-activity to an α-activity no less than 75% of the initial α-activity of the fresh, untreated zeolite-based catalyst. The catalyst, when treated in this manner, has enhanced stability over the fresh catalyst.

This invention is accomplished by presteaming or hydro-thermally treating a fresh zeolite catalyst under mild conditions until the activity of the mildly pretreated catalyst has been increased to a peak and then reduced to a level which is substantially equivalent to that of a fresh, unsteamed catalyst; adding the pretreated catalyst to a methanol-to-gasoline (MTG) conversion zone; and conducting a feedstock comprising lower aliphatic $C_1$-$C_4$ oxygenates to the MTG conversion zone at elevated temperatures and pressures to produce predominantly hydrocarbon products boiling in the gasoline range.

The siliceous crystalline zeolites used in such catalysts are generally members of a class of zeolites that exhibits unusual properties. Such zeolite materials are those which have a silica to alumina molar ratio of at least 12 and a constraint index within the range of 1 to 12. Zeolite materials of this type are well known. Crystalline zeolites of the type useful in the catalysts of the present invention include ZSM-5, ZSM-11, ZSM-12, ZSM-23, ZSM-35, ZSM-38 and ZSM-48, with ZSM-5 being particularly preferred.

ZSM-5 is described in greater detail in U.S. Pat. Nos. 3,702,886 (Argauer et al) and Re. 29,948 (Dwyer et al), which patents provide the X-ray diffraction pattern of ZSM-5.

ZSM-11 is described in U.S. Pat. No. 3,709,979 (Chu); ZSM-11.

ZSM-12 is described in U.S. Pat. No. 3,832,449 (Rosinski et al).

ZSM-23 is described in U.S. Pat. No. 4,076,842 (Rubin et al).

ZSM-35 is described in U.S. Pat. No. 4,016,245 (Plank et al).

ZSM-38 is described in U.S. Pat. No. 4,046,859 (Plank et al), which patents are incorporated herein by reference.

ZSM-48 is more particularly described in European Patent Publication No. EP-A-0015132 (Rollmann et al) which includes the X-ray diffraction pattern for ZSM-48.

When synthesized in the alkali metal form, the zeolite used to form the catalysts herein can be conveniently converted in a conventional manner to the hydrogen form, generally by intermediate formation of the ammonium form as a result of ammonium ion exchange and Calcination of the ammonium form to yield the hydrogen form of the zeolite, i.e. H-ZSM-5, prior to or after hydro-thermal treatment or pre-steaming. Other forms of the zeolite can be employed in the catalyst either prior to or after the pretreatment stabilization compositions herein. Suitable metal cations for exchange include Groups I through VIII of the Periodic Table, including, by way of example, nickel, copper, zinc, palladium, calcium or rare earth metals.

In preparing the zeolite-containing catalysts used in the present invention, the above-described siliceous crystalline zeolite material can be combined with an inorganic oxide binder or matrix comprising another material resistant to the temperature and other conditions employed in the conversion process.

The improvement over the prior art which forms the basis of the present invention is predicated upon the discovery that it is not necessary to severely reduce the activity of zeolite catalyst by steaming in order to obtain enhanced stability. It has been found that, by mildly presteaming a fresh zeolite catalyst under controlled conditions, the catalyst will initially exhibit an increase in activity followed by a gradual decline. When the activity of the catalyst becomes substantially similar to that of the fresh, unsteamed catalyst, the steam treatment is terminated. The steaming treatment is conducted at 5-100% steam, 300°-650° C., 101-2,500 kPa, and for 1-200 hours. In a preferred embodiment, the fresh zeolite catalyst undergoes steaming at 75-100% steam, 315°-400° C., atmospheric pressure, and for 10-25 hours. The final product has an α-activity of preferably from 100-300. The resulting catalyst has an activity level substantially similar to that of fresh, unsteamed catalyst together with improved stability.

When the zeolite catalyst of improved stability is prepared by thermal treatment of fresh unsteamed catalyst, the conditions are such that the steam partial pressure is adequate to increase the transient α-value about 15 to 40% above α at a temperature of at least 300° C. and treatment is continued until the α-value is not greater than α.

EXAMPLES 1-10

Table 1 illustrates the effect of very mild presteaming on fresh zeolite catalyst for use in methanol-to-gasoline conversion reactions. The catalyst employed in each example is HZSM-5 with a silica/alumina ratio of 70. In Table 1, α represents the degree of activity of the mildly steamed catalyst; $α_o$ represents the degree of activity of the fresh, unsteamed catalyst, and $α/α_o$ represents the degree in which α increases over or decreases below $α_o$.

As is well known in the art, the α-activity gives an approximate indication of the catalytic cracking activity of the catalyst compared to a standard catalyst and it gives the relative rate constant (rate of normal hexane conversion per volume of catalyst composition per unit time). It is based on the activity of the highly active silica alumina cracking catalyst taken as an α of 1. This test is described in U.S. Pat. No. 3,354,078 (Miale et al) and in *The Journal of Catalysis*, Vol. 4, pp. 522-529, August 1965. For purposes of the present invention, however, all measurements of α are to be made at 538° C. (1000° F.) and all references to α are to be understood to refer to the value obtained when the hexane cracking is measured at 538° C. (1000° F.).

Illustrated in FIG. 1 is the relationship of activity of the mildly presteamed catalyst to the steaming severity of the catalyst. The parameters for steaming severity are represented in Table 1. It is understood that the term "steaming severity" represents a proportional relationship between the length of time, the temperature, the partial pressure and the percent of steam in the steam treatment. As is shown in FIG. 1, an increase in steaming severity resulted in an increase in α-activity of the catalyst to a point of peak enhancement (represented by Example 3, Table 1). With continued increases in steaming severity, the α-activity decreased. At the level of severity represented by Example 5, Table 1, the α-activity of the catalyst was substantially equivalent to that of the fresh catalyst ($\alpha = 0.9 \ \alpha_o$). As can be readily seen from Examples 7-10, increased steaming severity further diminished the α-activity of the zeolite catalyst.

plotted against water partial pressure, with other variables such as treating time and temperature being held constant. With increasing water partial pressure, activity is continuously enhanced above initial relative activity until a point of maximum enhanced relative activity is attained.

$$\alpha_{MA}/\alpha_o$$

Once maximum enhanced relative activity is achieved, the activity begins to decrease with increasing water partial pressure, ultimately back to the same activity as the initial relative activity (same activity as the untreated zeolite, i.e. initial activity). Increasing water partial pressure after this return to initial activity will eventually result in catalyst deactivation (too severe conditions).

Catalyst activation occurs in a limited region of conditions which can be defined as a "zone of enhanced activity". This zone encompasses those conditions which yield activities greater than the initial activity ($\alpha_o$). Thus the zone is that area bounded by the activity of an untreated catalyst (initial activity) and the activity of the catalyst when it returns to the initial activity. In terms of relative activities, the zone of enhanced activity is that area bounded by the initial relative activity

TABLE 1

| | Effect of Steaming of HZSM-5 (atmospheric pressure) | | | | | | | | | |
|---|---|---|---|---|---|---|---|---|---|---|
| Example No. | 1 | 2 | 3 | 4 | 5 | 6 | 7 | 8 | 9 | 10 |
| Steam Treat (partial pressure) | None | 101 kPa | 101 kPa | 101 kPa | 101 kPa | 101 kPa | 101 kpa | 101 kPa | 101 kPa | 101 kPa |
| Hours | Fresh | 6 | 6 | 6 | 3 | 6 | 6 | 8 | 3.5 | 8 |
| Temp. (°C.) | Fresh | 202 | 257 | 312 | 422 | 422 | 450 | 464 | 532 | 546 |
| α | 160* | 240 | 380 | 360 | 148 | 130 | 82 | 60 | 33 | 20 |
| α/α$_O$ | 1 | 1.5 | 2.4 | 2.3 | 0.9 | 0.8 | 0.5 | 0.4 | 0.2 | 0.1 |

*α = α$_O$

The results of these experiments show that mild presteaming of a catalyst to place its α-activity past peak enhancement but no less than 75% and, preferably, within 10% of the initial α-activity is essential for a highly stable catalyst of high activity and selectivity.

The zeolite catalysts to be steamed according to the invention are generally those zeolites of at least 12 silica/alumina ratio and a constraint index of 1 to 12 which, in the acid form, have activity to convert lower molecular weight oxygenates to gasoline boiling range hydrocarbons. The degree of steaming should be such that the α-activity of the steamed catalyst should be less than the α-activity of the fresh, unsteamed catalyst but no greater than 25% less than the α-activity of the fresh catalyst and preferably no greater than 10% less.

The present invention involves using mild temperature presteaming to partially deactivate the catalyst. The deactivation should be conducted to a level such that the steamed catalyst activity is no less than 75% of the activity of the fresh, unsteamed catalyst and the process requires a maximum 14° C. rise in operating temperature, well below the minimum 28° C. rise referred to in U.S. Pat. No. 4,236,996 (Tabak et al). Additionally, the mildly presteamed catalyst demonstrates superior stability characteristics while maintaining catalytic activity substantially equivalent to that of fresh, unsteamed catalysts.

Figure 2:
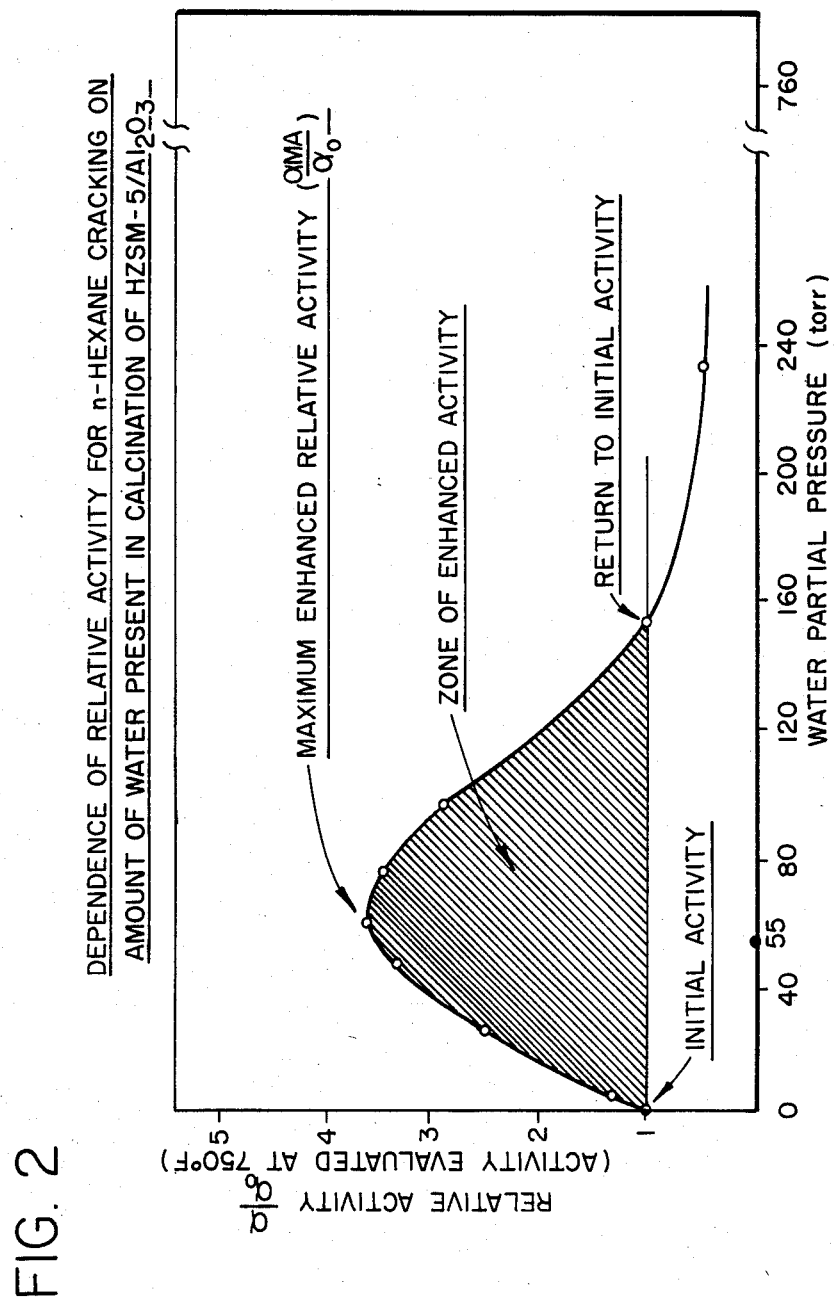
FIG. 2 illustrates the activity curve of a steamed acid zeolite catalyst with increasing partial pressure of water.

FIG. 2 depicts the activity curve over which the fresh catalyst passes when it is mildly steamed or hydrothermally treated. Relative activity of the catalyst is $$\frac{\alpha_o}{\alpha_o} = 1$$

and the return to initial relative activity $$\frac{\alpha}{\alpha_o} = 1$$

The zone of enhanced activity embraces all conditions and combinations thereof yielding activities greater than the initial catalyst activity. One such activity in this zone is the maximum activity. An expression to approximately define this band in relation to two specific variables-treating time and water partial pressure, with temperature held constant is as follows:

$$0.01(Pt)_T < (Pt) < 10(Pt)_T$$

where
 $(Pt)_T = 2.6 \times 10^{-9} e^{16000/T}$
 P = Water Partial Pressure, atmospheres
 t = Treating Time, hours
 T = Temperature, °K.

In the present invention the fresh unsteamed zeolite catalyst is mildly presteamed or hydro-thermally treated so that the relative activity passes through the "zone of enhanced activity" to reach a final value less than, but close to, unity.

A comparison of the aging characteristics of various presteamed zeolite catalysts when employed in the methanol-to-gasoline (MTG) process is given in Table II. The duration of catalyst activity in the MTG process is experimentally determined as follows: the catalyst sample is maintained in a fixed-bed reactor at a temperature of about 440° C. and a pressure of about 2060 kPa. A feedstock comprising a mixture of helium carrier gas and methanol in a molar ratio of 9:1 is passed over the catalyst sample at a weight hourly space velocity of about 4 hr$^{-1}$. The reaction is continued until methanol is observed in the product. This methanol "breakthrough" determines the catalytic cycle length of the sample catalyst.

Zeolite catalysts having a silica-to-alumina ratio of from 47 to 70 are taken in their fresh state and presteamed at atmospheric pressure and in the presence of saturated steam at various conditions of temperature and time. In most cases the α-activity of the steamed zeolite catalyst is equal to or below the α-activity of the fresh catalyst. The steamed catalysts exhibit increased aging characteristics as compared to the fresh catalysts, yet they retain a substantial amount of catalytic activity.

TABLE II

| Zeolite SiO$_2$/Al$_2$O$_3$ | α-Value of Fresh Catalyst | Atmospheric Pressure, 100% Steam | | | Duration of Catalyst Activity in MTG Process (days) |
|---|---|---|---|---|---|
| | | Steaming Temperature (°C.) | Steaming Time (hrs.) | α-value of Steamed Catalyst | |
| 70 | 180 | 332 | 16 | 333 | 6 |
| 70 | 180 | 388 | 14 | 180 | 8.4 |
| 55 | 200 | 332 | 19 | 200 | 4.5 |
| 55 | 200 | 388 | 18 | 172 | 5.5 |
| 47 | 220 | 332 | 16 | 205 | 5.5 |
| 47 | 220 | 388 | 8 | 218 | 6 |
| 47 | 220 | 416 | 2 | 144 | 6.5 |

The major importance of this development relates to the use of zeolite catalysts, particularly ZSM-5, in the conversion of alcohols to hydrocarbons such as methanol to gasoline. In a preferred embodiment, the feedstock comprises methanol, dimethylether, or mixtures thereof and the conversion process is conducted at a temperature of about 300° C. to 650° C. and pressure of at least 800 kPa to produce predominantly aromatic gasoline. Such a reaction would preferably incorporate a catalyst with the unique qualities of stabililty and catalytic activity similar to fresh, unsteamed catalysts.

For such use it is possible to combine the zeolites of the present invention with metal promoters such as Zn, ZnPd, Pt, Cr, etc. Such promoters may be incorporated with the zeolite in accordance with the ion exchange technique or by other techniques such as impregnation. Incorporation of such metal promoters can occur either before or after the zeolite catalysts are steamed or hydro-thermally treated in accordance with the present invention.

We claim:

1. A process for converting lower aliphatic C$_1$–C$_4$ oxygenates to gasoline range hydrocarbon products comprising the steps of:
    pretreating a catalyst comprising a zeolite having a silica/alumina ratio greater than 12 and a constraint index of 1 to 12 by steaming the zeolite catalyst in its fresh state under controlled conditions of temperature, time and steam partial pressure so as to initially increase the α-activity of the catalyst and produce a steamed catalyst having a peak α-activity, and subsequently reduce the α-activity from the peak α-activity to an α-activity substantially the same as the α-activity of the fresh catalyst and no more than 25% below the initial α-activity of the fresh catalyst, the pretreated catalyst being more stable than the fresh catalyst;
    adding the pretreated catalyst to a methanol-to-gasoline (MTG) conversion zone; and
    conducting a feedstock comprising lower aliphatic C$_1$–C$_4$ oxygenates to the MTG conversion zone at elevated temperatures and pressures to produce hydrocarbon products boiling in the gasoline range.

2. In a process for converting lower aliphatic C$_1$–C$_5$ oxygenates to gasoline range hydrocarbon products by contacting the oxygenates at elevated temperatures and pressures with a crystalline zeolite catalyst having acid cracking activity, the improvement which comprises:
    pretreating the zeolite catalyst by steaming the catalyst in its fresh state under controlled conditions of temperature, time and steam partial pressure so as to initially increase the α-activity of the catalyst and produce a steamed catalyst having a peak α-activity, and subsequently reduce the α-activity from the peak α-activity to an α-activity substantially the same as the α-activity of the fresh catalyst and no more than 25% below the initial α-activity of the fresh catalyst, the pretreated catalyst being more stable than the fresh catalyst.

3. The process of claim 1 wherein the zeolite pretreatment is conducted at a steam partial pressure adequate to increase the α-transient value about 15 to 40% above α$_o$ at a temperature of at least 300° C. and treatment is continued until the α-value is not greater than α$_o$.

4. The process of claim 1 wherein the zeolite catalyst consists essentially of HZSM-5.

5. The process of claim 4 wherein the feedstock comprises methanol, dimethylether, or mixtures thereof and wherein the conversion process is conducted at a temperature of about 300° C. to 650° C. and pressure of at least 800 kPa to produce predominantly aromatic gasoline.

6. The process of claim 3 wherein the steaming treatment is conducted at a temperature of about 315° C. to 400° C. and at a steam partial pressure of about atmospheric to 2500 kPa.

7. In the process of converting a lower aliphatic C$_1$–C$_4$ oxygenate feedstock to predominantly liquid hydrocarbons by contacting the feedstock at elevated conversion process temperature with acid metallosilicate medium pore zeolite catalyst with a silica to metal oxide molar ratio of at least 20:1 to provide Brönsted acid activity and a constraint index of about 1 to 12; the improvement which comprises:
    employing a thermally-stabilized zeolite catalyst comprising the medium pore zeolite having been pretreated hydro-thermally in the substantial absence of lower aliphatic oxygenates to increase acid activity from an initial fresh catalyst acid value to a peak acid value and further hydro-thermally treated to decrease acid activity from the peak value to about the initial acid value, thereby increasing catalyst life during the conversion process.

8. A method for producing liquid hydrocarbons from lower aliphatic oxygenate feedstock under elevated temperature and pressure oxygenate conversion process conditions employing an acidic ZSM-5 type aluminosilicate zeolite catalyst, said zeolite catalyst being prepared by hydro-thermally treating fresh aluminosilicate zeolite having a silica to alumina molar ratio of about 20:1 to 200:1 to increase the initial acid cracking value ($\alpha_o$) by transient activation and decreasing the $\alpha$-value to about that of the fresh catalyst in the range of about $100\alpha$ to $300\alpha$, said thermal treatment being conducted in the absence of lower aliphatic oxygenates; and charging oxygenate feedstock to a conversion zone containing the hydro-thermally treated zeolite catalyst at elevated temperature and pressure under process conditions to produce predominantly gasoline range liquid hydrocarbon product, the catalyst having increased duration of stable activity and resistance to aging.

9. The method of claim 8, wherein the hydro-thermal zeolite treatment is conducted at a steam partial pressure adequate to increase the $\alpha$-transient value about 15 to 40% above $\alpha_o$ at a temperature of at least 300° C. and treatment is continued until the $\alpha$-value is not greater than $\alpha$.

10. The method of claim 9 wherein the zeolite catalyst consists essentially of HZSM-5.

11. The method of claim 10 wherein the feedstock comprises methanol, dimethylether, or mixtures thereof and wherein the conversion process is conducted at a temperature of about 300° C. to 650° C. and pressure of at least 800 kPa to produce predominantly aromatic gasoline.

12. The method of claim 9 wherein the hydro-thermal treatment is conducted at a temperature of about 315° C. to 400° C. and at a steam partial pressure of about atmospheric to 2500 kPa.

* * * * *